United States Patent
Weber et al.

(10) Patent No.: US 11,959,570 B1
(45) Date of Patent: Apr. 16, 2024

(54) EXAMINATION ROOM HAVING CT INSTALLATION WITH IMPROVED CABLE GUIDANCE

(71) Applicant: Siemens Healthcare GmbH, Erlangen (DE)

(72) Inventors: Moritz Weber, Nuremberg (DE); Wolfgang Neuber, Eschenbach I. D. Opf. (DE); Jan-Christoph Kiesel, Bayreuth (DE)

(73) Assignee: SIEMENS HEATHINEERS AG, Forchheim (DE)

( * ) Notice: Subject to any disclaimer, the term of this patent is extended or adjusted under 35 U.S.C. 154(b) by 0 days.

(21) Appl. No.: 18/476,639

(22) Filed: Sep. 28, 2023

(30) Foreign Application Priority Data

Sep. 29, 2022 (DE) ...................... 10 2022 210 342.4

(51) Int. Cl.
*A61B 6/00* (2006.01)
*A61B 6/03* (2006.01)
*F16L 3/015* (2006.01)

(52) U.S. Cl.
CPC .............. *F16L 3/015* (2013.01); *A61B 6/035* (2013.01)

(58) Field of Classification Search
CPC ........................................................ A61B 6/35
See application file for complete search history.

(56) References Cited

U.S. PATENT DOCUMENTS 5,305,363 A * 4/1994 Burke ...................... H05G 1/60
378/10
2014/0037071 A1* 2/2014 Foerner ................ A61B 6/4435
378/193

FOREIGN PATENT DOCUMENTS

DE    102012213875 A1    2/2014
DE    202019105377 U1    10/2019

OTHER PUBLICATIONS

German Office Action and English translation thereof dated Jun. 20, 2023.

* cited by examiner

*Primary Examiner* — Dani Fox
(74) *Attorney, Agent, or Firm* — Harness, Dickey & Pierce, P.L.C.

(57) ABSTRACT

Arranged in an examination room is a CT installation which can travel along a predetermined travel path between two installation limit positions. Arranged on the CT installation is a telescopic rod, which extends from a hinge point that is proximal with respect to the CT installation to a hinge point that is distal with respect to the CT installation. The telescopic rod is rotatably mounted in the two hinge points, and can telescope between a minimum length and a maximum length. Arranged on the telescopic rod (6) are a number of retaining elements that can travel along the telescopic rod. A number of lines are guided via the retaining elements, so that when the telescopic rod is of minimum length, the lines are guided in serpentine loops.

20 Claims, 13 Drawing Sheets

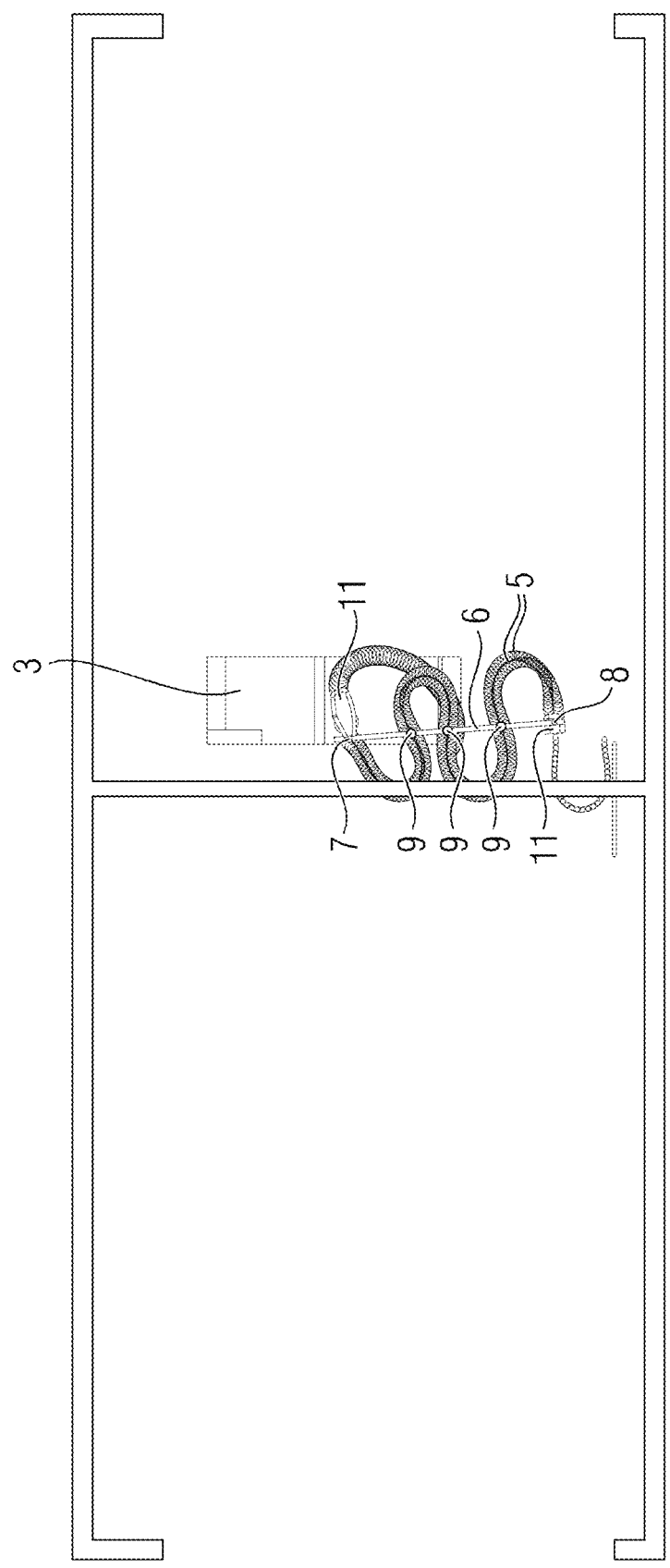

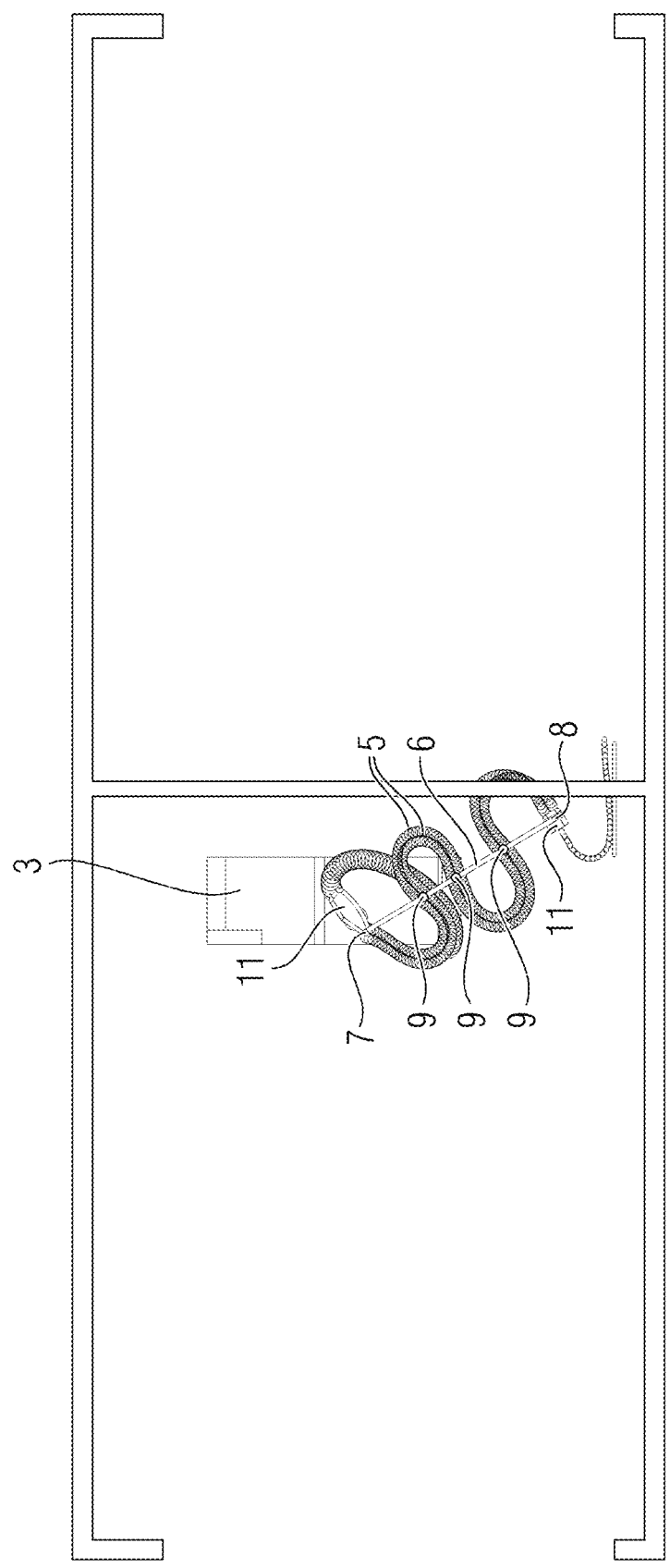

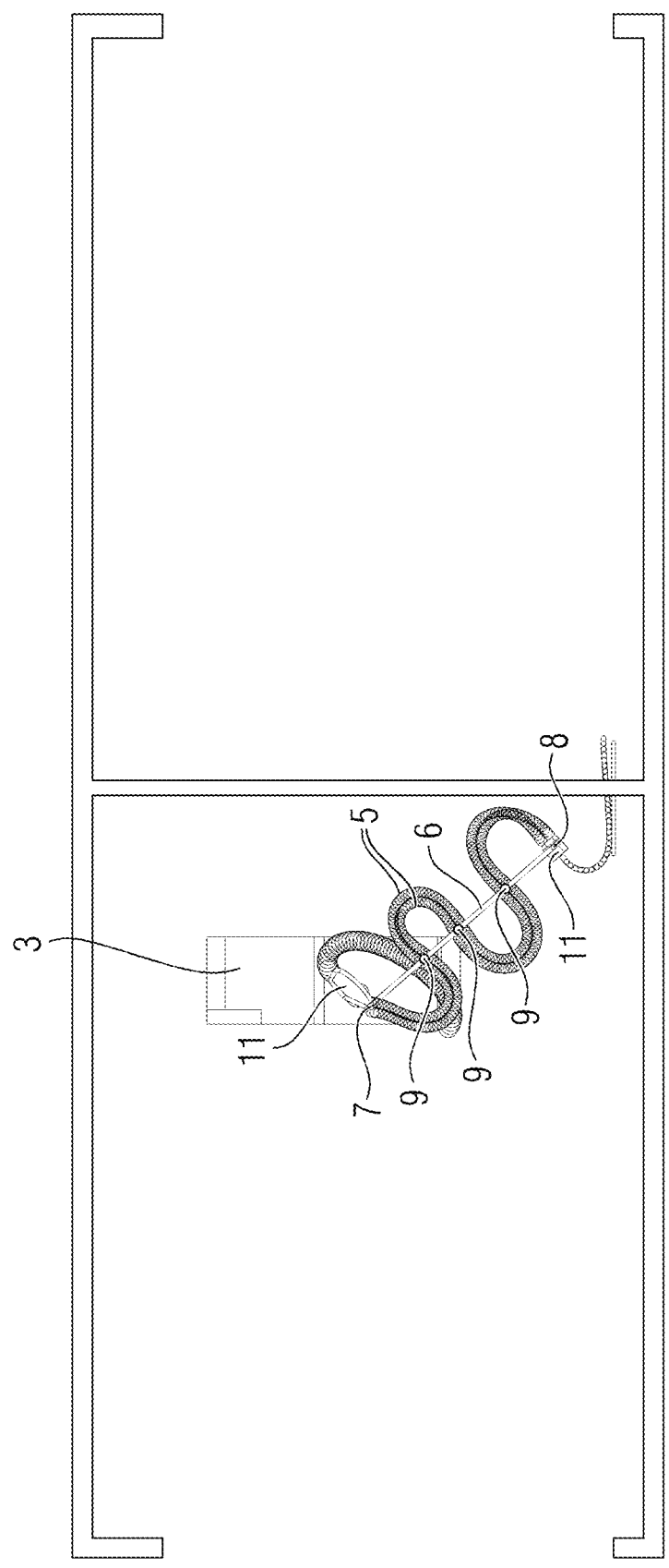

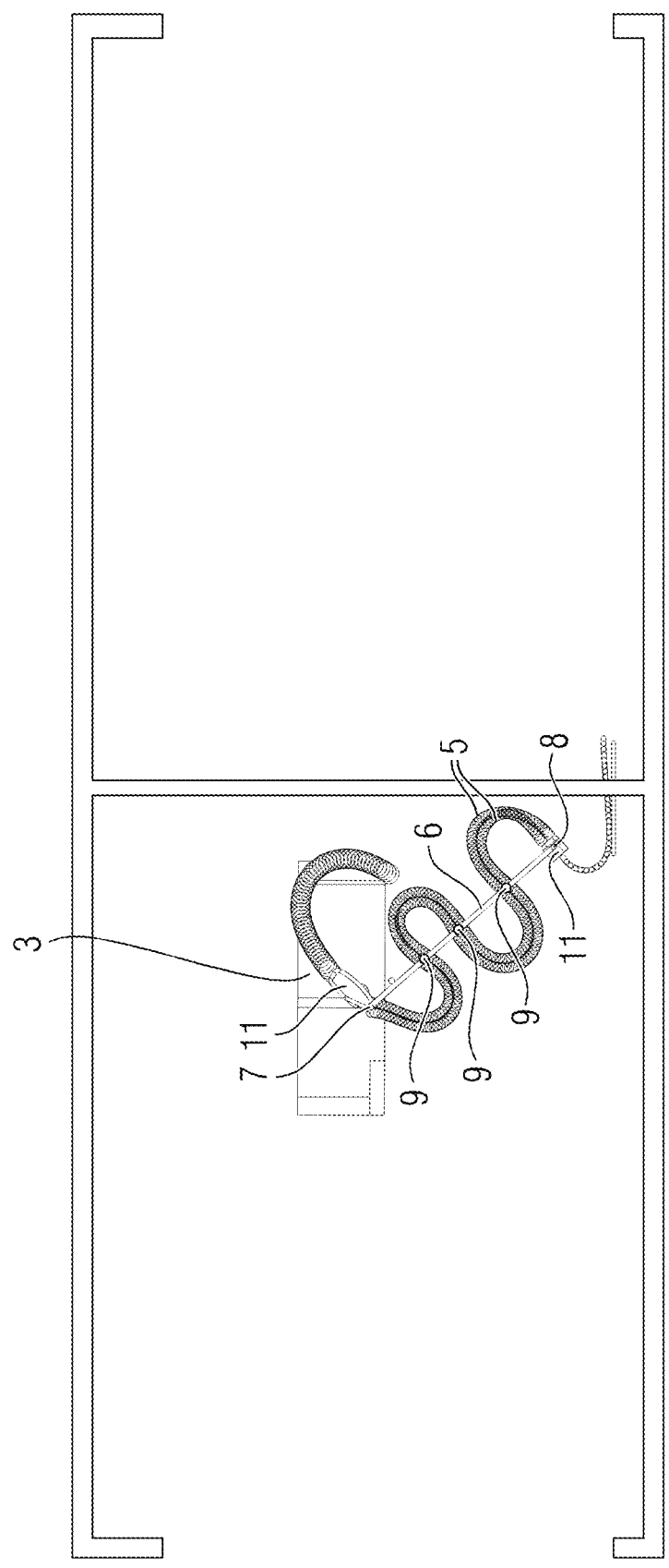

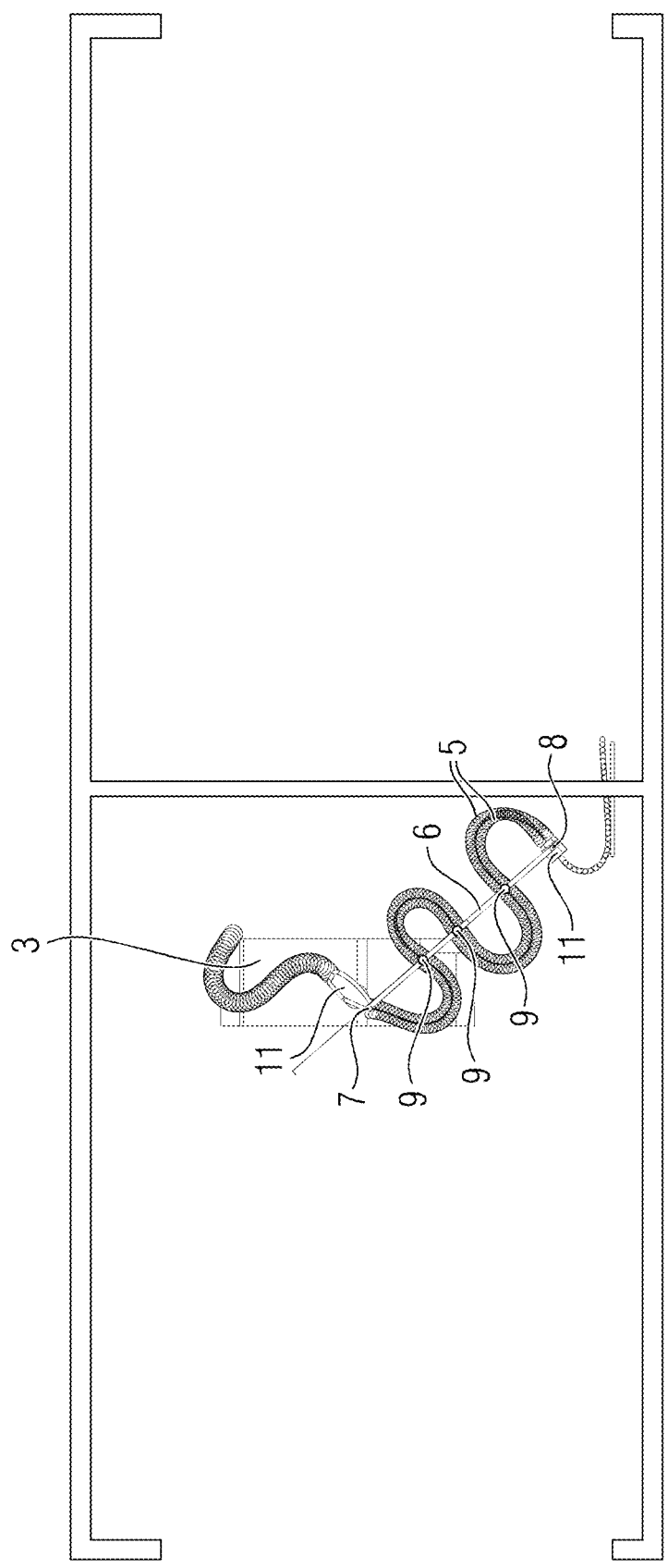

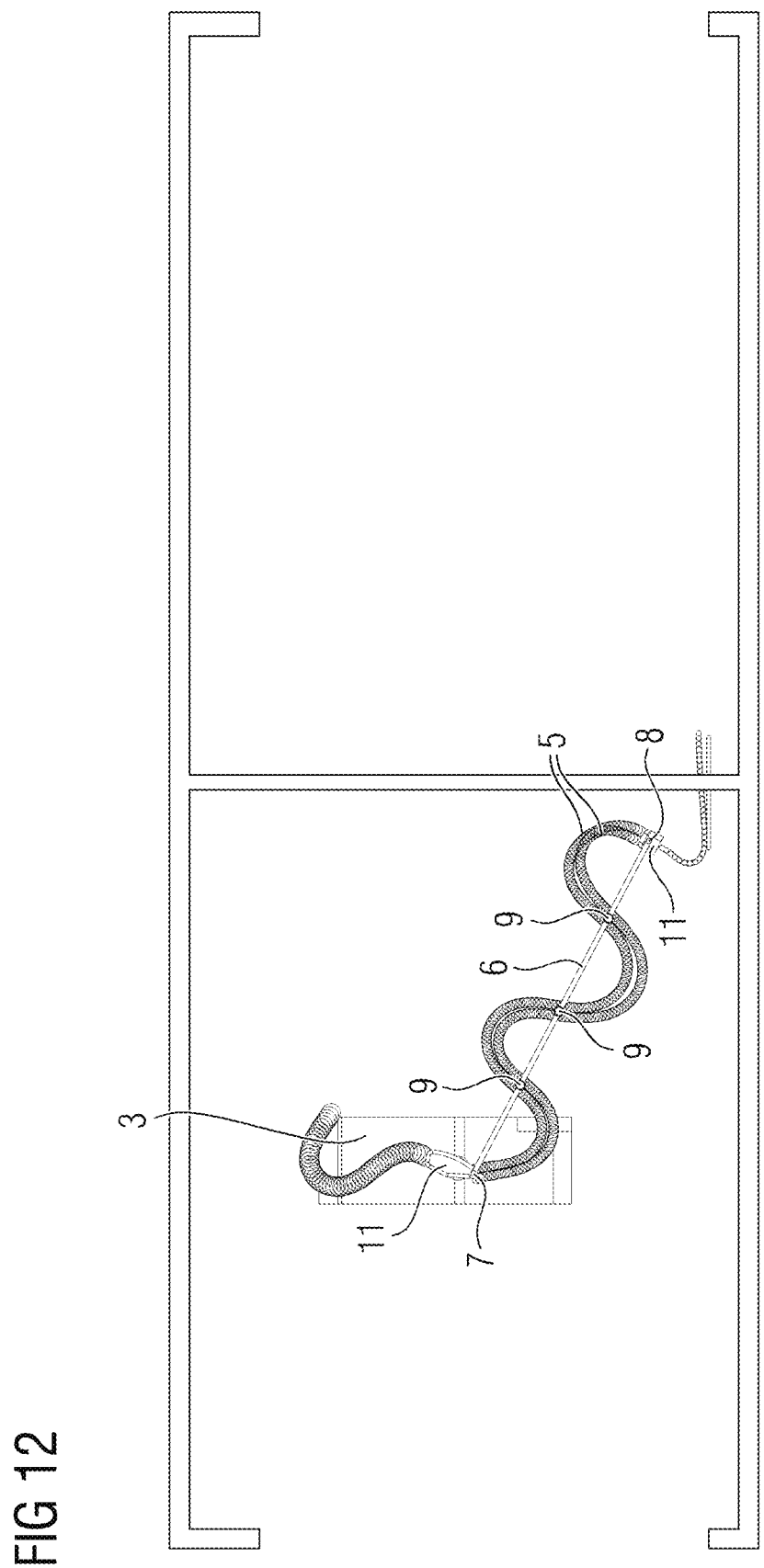

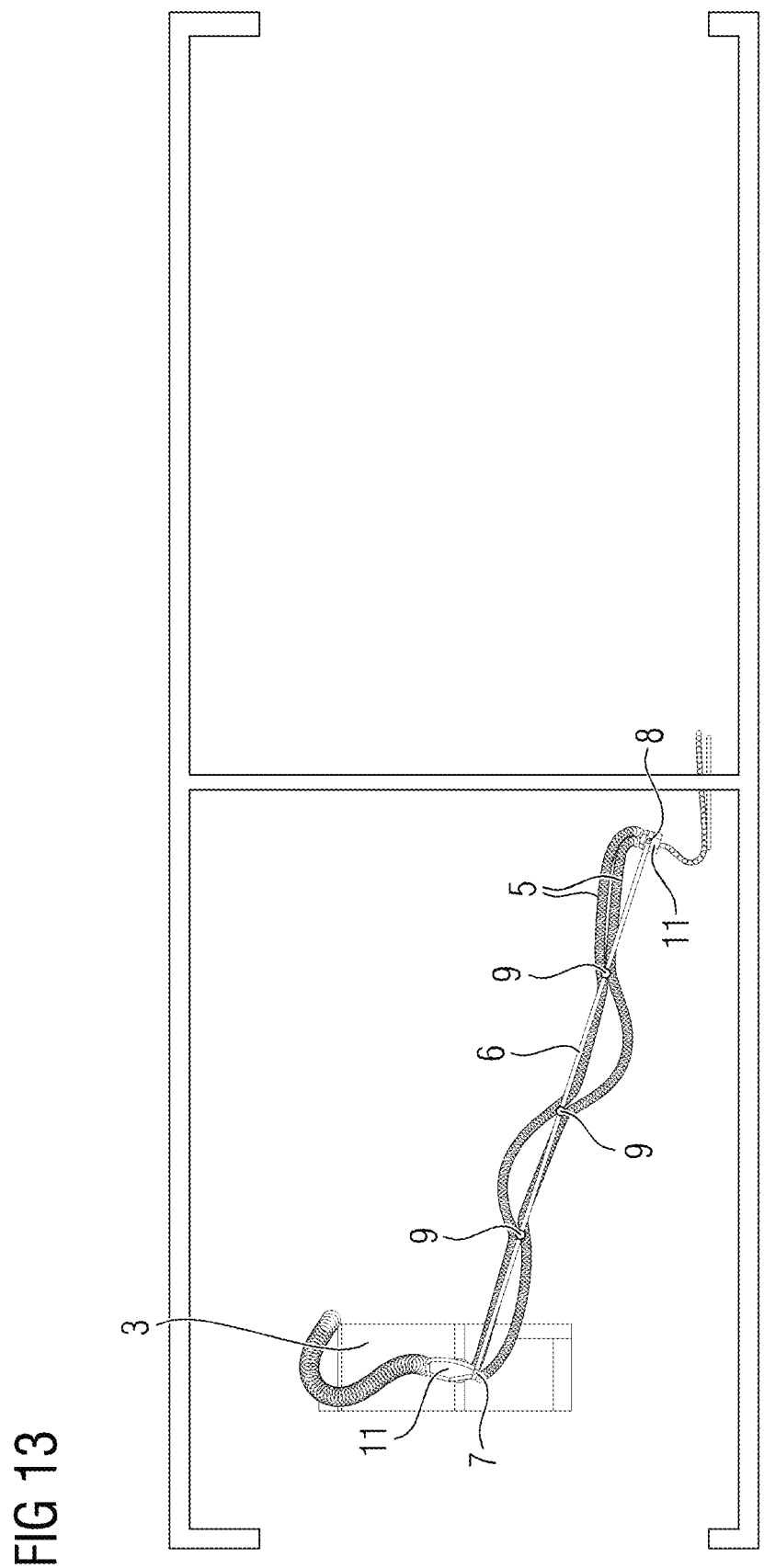

EXAMINATION ROOM HAVING CT INSTALLATION WITH IMPROVED CABLE GUIDANCE

CROSS-REFERENCE TO RELATED APPLICATION(S)

The present application claims priority under 35 U.S.C. § 119 to German Patent Application No. 10 2022 210 342.4, filed Sep. 29, 2022, the entire contents of which are incorporated herein by reference.

FIELD

One or more example embodiments of the present invention is based on an examination room,
wherein arranged in the examination room is a CT installation which can travel along a predetermined travel path between two installation limit positions.

RELATED ART

In the context of the present invention, the term "room" is not used in the sense of an undefined space but in the sense of a relatively large room. The travel path of the CT installation can be defined by rails, for example, along which the CT installation can travel. Usually the travel path is linear. A curved course of the travel path (in particular a semicircular course or two quarter-circle shaped courses) shall not be ruled out, however. The installation limit positions are the limit positions of the travel path of the CT installation. Specifying the limit positions as installation limit positions is merely a means of distinguishing linguistically from hinge-point limit positions, which will be introduced later, but otherwise has no further significance.

Such examination rooms are generally known. They are used in particular in the medical sector for examining people.

Movable CT installations (CT=computed tomography) are being used increasingly in modern medical examination and treatment facilities. The primary purpose of the mobility of the CT installations is for shifting the CT installations, which typically are large and occupy a large amount of room, in order to be able to provide space in the immediate vicinity of the patient for medical personnel and/or further installations or devices that are used for an examination, a treatment and/or an intervention. The focus here is the wellbeing and safety of the patient and also of the operating personnel. The operational safety of the machines (for example the CT installation) is also important.

In addition, mobility of the CT installations also makes it possible to use one and the same CT installation in different treatment rooms, and hence to reduce investment and maintenance costs in the long term.

It is known to shift CT installations along rails so that the CT installations can travel along a travel path predefined by the rails. Alternatively, freely movable CT installations are also known. Whereas freely movable CT installations have a rechargeable on-board energy supply, for instance in the form of a lithium-ion storage device, as a rule the supply for rail-mounted systems is by wired means.

For CT installations that are used in different, typically two, treatment rooms, the associated cable guidance systems must be designed to be movable and flexible, and in such a way that they can span distances of several meters, for example up to 12 m. The mechanical strain, however, must not impair the working life of the cable guidance system.

Moreover, it must be ensured that the cable guidance system itself cannot cause collisions with the patient, medical personnel and surrounding devices during any movement when shifting the CT installation.

For example, solutions for cable guides are accordingly provided in the prior art that are arranged in the floor, typically close to the rail system. Collisions are largely ruled out in this case. These solutions, however, require structural preconditions for the hospital environment, and therefore cannot be used without constraints. In addition, often they do not conform to the hygiene requirements of a medical environment, and are expensive.

Alternatively, solutions are known in which supply lines are arranged in a ceiling box via one or more cable chains. In this case, the rail system runs parallel to the longitudinal axis of the ceiling box. In this embodiment, a vertical pillar is present on the gantry of the CT installation and moves jointly therewith, and through which the supply lines are guided downwards to the base of the gantry, where they are connected. The length of the ceiling box, however, must extend over the entire travel path of the CT installation, and, because of the finite radius of curvature of the energy chain, normally even a bit further. Therefore the ceiling box occupies a considerable amount of installation space that hence cannot be otherwise used. It can also happen that the laminar air flow, which is meant to be maintained in particular in the region of a patient, is disturbed. This embodiment is also unsightly.

SUMMARY

The object of the present invention is to create alternative opportunities for cable guidance for a movable CT installation, which facilitate greater movement flexibility with a long working life and low construction costs. In particular, it is the object of the present invention to increase the freedom of movement of a cabled and rail-mounted CT installation to such an extent that it can be used in different treatment rooms with an opposite operating direction.

The object is achieved by an examination room having the features of claim 1. The subject matter of dependent claims 2 to 9 contains advantageous embodiments of the examination room.

BRIEF DESCRIPTION OF THE DRAWINGS

The following description of the exemplary embodiments, which are explained in greater detail in connection with the drawings, will clarify and elucidate the above-described properties, features and advantages of this invention, and the manner in which they are achieved, in which drawings, in a schematic representation:

FIGS. 4 to 13 show the travel of the CT installation from a first installation limit position to a second installation limit position according to one or more example embodiments.

DETAILED DESCRIPTION

Figure 1:
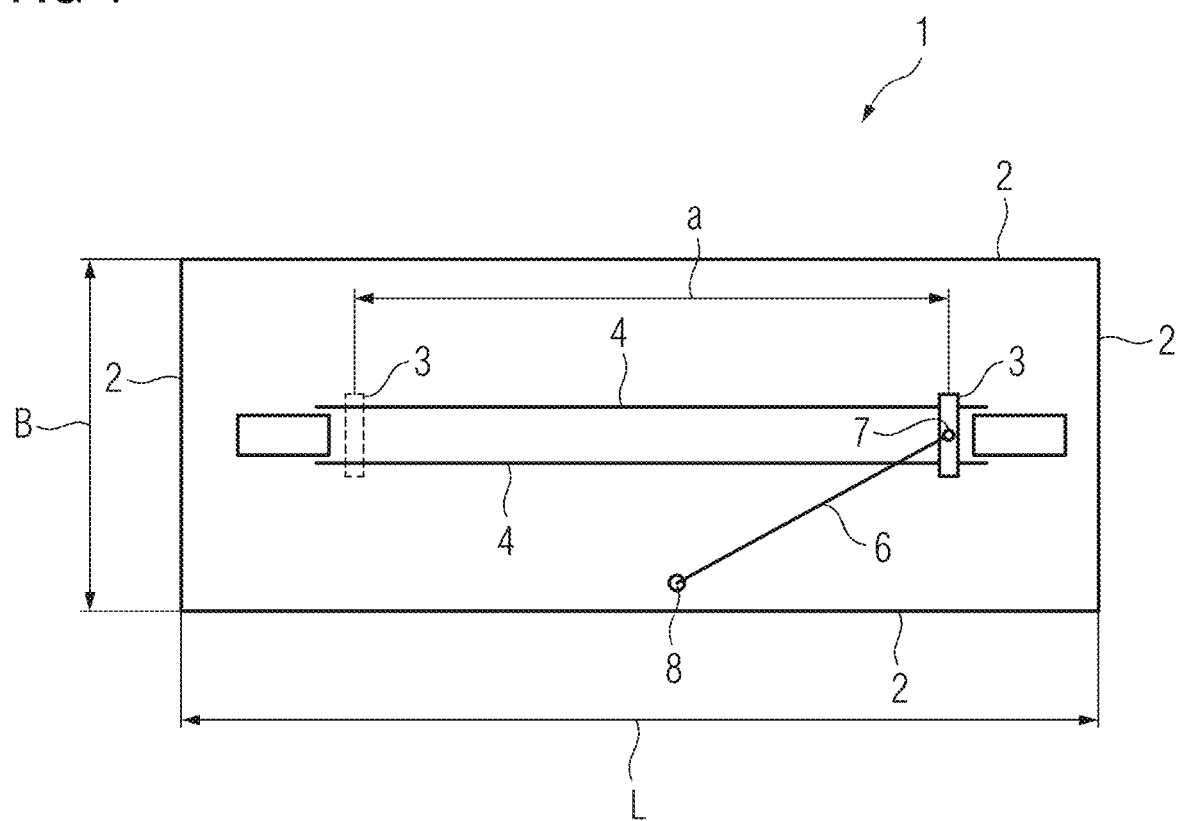
FIG. 1 shows an examination room from above according to one or more example embodiments.

According to one or more example embodiments of the present invention, an examination room of the type mentioned in the introduction is embodied such that arranged on the CT installation is a telescopic rod, which extends from a hinge point that is proximal with respect to the CT installation to a hinge point that is distal with respect to the CT installation, the telescopic rod is rotatably mounted in the two hinge points and can telescope between a minimum length and a maximum length, arranged on the telescopic rod are a number of retaining elements that can travel along the telescopic rod, and a number of lines are guided via the retaining elements, so that when the telescopic rod is of minimum length, the lines are guided in serpentine loops.

The proximal hinge point is the hinge point arranged closer to the CT installation; the distal hinge point is the hinge point further away from the CT installation. The telescopic rod extends between the two hinge points but not, or at least not to any significant extent, beyond the two hinge points.

The number of retaining elements can be according to need. A single retaining element is present as a minimum. Usually, however, a plurality of retaining elements are present. The number of retaining elements is normally in the single-digit range, thus equals a maximum of 9. Often, the number of retaining elements lies even in the lower single-digit range, thus equals a maximum of 5.

The retaining elements can be free-running. In this case, they are not assigned a drive. The retaining elements in this case adopt positions as a result of the forces acting externally on the retaining elements. Alternatively, the retaining elements can be driven. In this case, setpoint values for the drives of the retaining elements are determined according to the position of the CT installation along its travel path. The position of the CT installation can be its actual position. In the case of motorized travel of the CT installation, the position can also be its setpoint position. Similar to the retaining elements, the telescopic rod itself can also be free-running or driven.

The number of lines can be according to need. A single line is present as a minimum. Normally, however, a plurality of lines are present.

The extent to which the lines form loops is smaller the further the telescopic rod is extended. At the maximum length of the telescopic rod, the loops can be fully or almost stretched out.

According to need, the lines can comprise supply lines for electrical energy and/or gaseous and/or liquid media and/or electrical and/or optical signal and/or data lines. As a rule, at least the supply lines for electrical energy are present. The other lines, for example for a flow and return of cooling water for cooling components of the CT installation, or signal lines for transferring control signals to the CT installation, or data lines for transferring data captured by the CT installation, may or may not be present depending on the individual situation.

The lines are preferably guided in an energy chain having a multiplicity of chain links. The lines are thereby very well protected from mechanical influences.

An energy chain (also known as a drag chain, cable chain or cable carrier), is a mechanical chain which encloses an elongated cavity in the circumferential direction over at least 180°, better over at least 270°, optimally over 360°, so that lines running in the cavity are protected from mechanical influences. Energy chains are widely used in mechanical engineering and are known and familiar to persons skilled in the art. The chain links can move in at least one direction with respect to both the preceding and succeeding chain link, as is the case for every chain.

Energy chains are made by numerous manufacturers. Reference can be made purely by way of example to the energy chains from the company igus GmbH, Spicher Str. 1a, 51147, Cologne (Germany).

Preferably, the retaining elements each retain at least one chain link of the energy chain, and the relevant chain links are immovably arranged in the respective retaining elements. This results in especially reliable guidance of the lines, in particular in long-term operation.

The distal hinge point is preferably fixed with respect to the examination room. Alternatively, the distal hinge point can be able to travel parallel to the travel path of the CT installation between two hinge-point limit positions. In this case, however, a distance of travel between the two hinge-point limit positions is smaller than a distance of travel between the two installation limit positions.

A fixed arrangement simplifies the structural design. An ability to travel between the two hinge-point limit positions increases the possible travel path of the CT installation without a change to the telescopic rod. Furthermore, in this case the shielding of the particular region of the examination room in which the CT installation is currently arranged with respect to the remaining region of the examination room can be simpler.

The hinge-point limit positions are the limit positions of the travel path of the distal hinge point. Specifying these limit positions as hinge-point limit positions is merely a means of distinguishing linguistically from the installation limit positions, which have already been introduced, but otherwise has no further significance.

In many cases, one of the two installation limit positions is a parked position of the CT installation, the other a working position. In this case, the distal hinge point, whether or not it is itself able to travel, can be arranged beyond the parked position of the CT installation, so that the telescopic rod is not oriented orthogonal to the direction of travel of the CT installation at any point in time during travel of the CT installation from the one installation limit position to the other. Preferably, however, the distal hinge point, whether or not it is itself able to travel, is located between the two installation limit positions of the CT installation. This still applies when one of the two installation limit positions is a parked position for the CT installation and only the other installation limit position is a working position. This is because this embodiment, i.e. the arrangement between the two installation limit positions of the CT installation, allows a more compact construction of the examination room. If both installation limit positions are working positions of the CT installation, this embodiment simplifies operation of the CT installation in its two limit positions.

It is possible that the lines run parallel to the telescopic rod in the region of the retaining elements. If the course of the lines is visualized as a wave having a plurality of wave peaks and a plurality of wave troughs, then, with the telescopic rod retracted, the retaining elements would thus be located in this case in the region of the wave peaks. In this case, the retaining elements could be arranged in a fixed (non-rotatable) manner on the telescopic rod. Preferably, however, the lines cross the telescopic rod in the region of the retaining elements, and furthermore the retaining elements are rotatably arranged on the telescopic rod. If the course of the lines is visualized as a wave having a plurality of wave peaks and a plurality of wave troughs, then, with the telescopic rod retracted, the retaining elements would thus be located in the region between the wave peaks and wave troughs, preferably exactly or approximately in the center between the wave peaks and the wave troughs.

Further retaining elements are preferably arranged in the two hinge points. The further retaining elements can be arranged in a rotatable or alternatively fixed manner on the telescopic rod. The further retaining elements simplify the guidance of the lines beyond the two hinge points.

In the case of a fixed arrangement, the angles that the further retaining elements form with the telescopic rod are determined according to need. Usually the angles are greater than 60°, mostly even greater than 75°. In particular, the angles can be at least 85°, for example exactly 90°.

Between the two installation limit positions, the CT installation is preferably able to rotate about a vertical axis. In the case of this embodiment, both installation limit positions can be working positions of the CT installation despite a relatively short travel path of the CT installation. The rotation is preferably a rotation through 180°. The vertical axis preferably runs through the isocenter of the CT installation.

The lines preferably extend from the proximal hinge point in a further loop to an end point that is fixed with respect to the CT installation. This embodiment in particular simplifies the implementation of the capability of the CT installation to rotate about its vertical axis. As a rule, the further loop is a continuation of the loops between the two hinge points. There can be a similar embodiment for the distal hinge point, if required.

According to FIG. 1, an examination room 1 (for example an operating theater) is bounded by outer walls 2. FIG. 1 does not show doors or any windows; nor does it show any fixed or movable dividing walls for partitioning the examination room 1. The examination room 1 often has a length L in the 2-digit meter range, for instance between approximately 20 m and approximately 25 m. A width B normally has a smaller value, for instance equals approximately 10 m. The stated dimensions L, B are purely by way of example, however.

A CT installation 3 is arranged in the examination room 1. The CT installation 3 can travel along a predetermined travel path between two installation limit positions. FIG. 1 shows the CT installation in continuous lines in the one installation limit position, and in dashed lines in the other installation limit position. The two installation limit positions often have a separation a of approximately 10 m. The separation a can also be larger, for instance up to 15 m. The travel path of the CT installation 3 between the two installation limit positions can be determined by rails 4, for example.

The CT installation 3 must be supplied at least with electrical energy when it is in operation. The supply of electrical energy is performed via suitable electrical supply lines 5a. Electrical supply lines 5a are thus required in practically all cases. The electrical supply lines 5a are not shown in FIG. 1 but shown only in FIG. 2.

In some cases, it is also necessary to feed (at least) one liquid or gaseous medium to the CT installation 3 while it is in operation, and, if applicable, to remove said medium again, for example to implement a cooling water circuit. Media supply lines 5b are needed if media are being fed and, if applicable, also removed. The media supply lines 5b are likewise shown only in FIG. 2 but not in FIG. 1.

It is also necessary for control signals to be transferred from a control facility to the CT installation 3, and for data captured by the CT installation 3 to be transferred to an analysis facility, with neither the control facility nor the analysis facility being part of the CT installation 3 itself, i.e. of the unit that can travel between the two installation limit positions. Control signals and data can be transferred wirelessly or alternatively via electrical or optical lines (shown neither in FIG. 1 nor in FIG. 2).

No distinction is drawn below between the electrical supply lines 5a, the media supply lines 5b and the electrical or optical lines for the transfer of control signals and data. Instead, the reference sign 5 is always used to refer only to lines in general. Thus according to need, the lines 5 can be electrical supply lines 5a, media supply lines 5b, control lines and data lines, with any combinations also being possible in principle.

Figure 2:
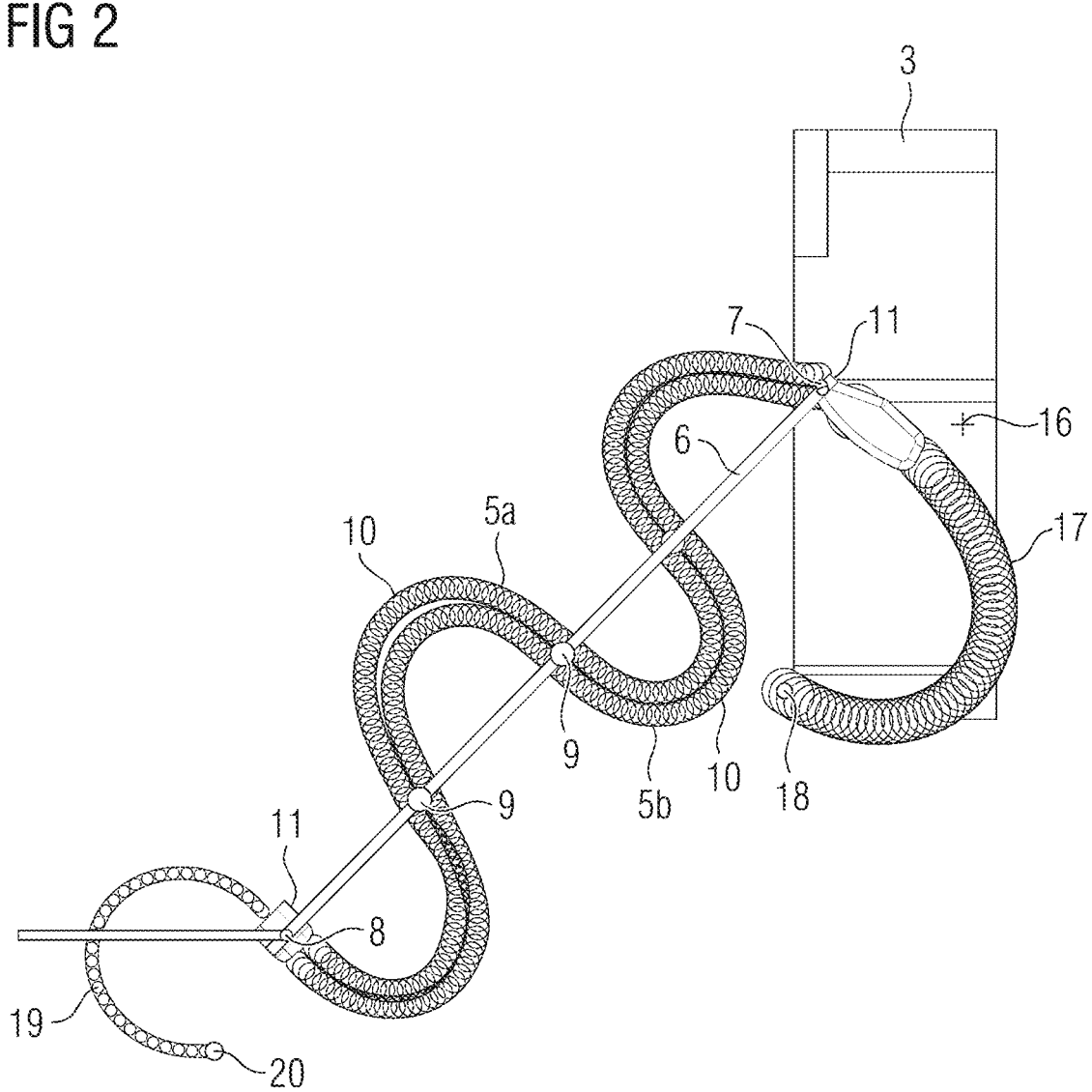
FIG. 2 shows a CT installation and an associated line guidance system according to one or more example embodiments.

For the purpose of guiding the lines 5, a telescopic rod 6 is arranged on the CT installation 3 as shown in FIG. 1 and FIG. 2. The telescopic rod 6 extends from a proximal hinge point 7 to a distal hinge point 8. The proximal hinge point 7 and the distal hinge point 8 are defined with respect to the CT installation 3. The proximal hinge point 7 is thus arranged closer to the CT installation 3 than is the distal hinge point 8. The proximal hinge point 7 can be arranged in a bridge element, for example, which spans the gantry of the CT installation 3. Alternatively, the proximal hinge point 7 can be arranged, for example, on the top end of a pillar arranged beside the gantry of the CT installation 3 and extending beyond the gantry of the CT installation 3.

The telescopic rod 6 is rotatably mounted in the two hinge points 7, 8, and can telescope between a minimum length and a maximum length. This will become evident from the explanations for FIGS. 4 to 13. Depending on how many elements that the telescopic rod 6 comprises that can be displaced relative to one another, a ratio between the maximum length and the minimum length of the telescopic rod 6 can equal, for example, up to 2:1, up to 3:1, up to 4:1 and even values that are even greater.

Arranged on the telescopic rod 6 shown in FIG. 2 are a number of retaining elements 9. The retaining elements 9 can travel along the telescopic rod 6. The ability of the retaining elements 9 to travel can be active (by motor) or alternatively passive. The ability of the retaining elements 9 to travel will become evident also from the explanations for FIGS. 4 to 13.

The lines 5 are guided via the retaining elements 9. At least for the minimum length of the telescopic rod 6, the lines 5 form serpentine loops 10. The further the telescopic rod 6 is extended, the more the loops 10 are stretched out. At the maximum length of the telescopic rod 6, the loops 10 can either be present to a small extent or can be fully stretched out. It is normally preferable if a small residual loop shape still exists.

According to FIG. 2, the lines 5 cross the telescopic rod 6 in the region of the retaining elements 9. Therefore the retaining elements 9 are rotatably arranged on the telescopic rod 6. The ability of the retaining elements 9 to rotate will become evident also from the explanations for FIGS. 4 to 13.

Usually there are further retaining elements 11 arranged in the two hinge points 7, 8. The further retaining elements 11 can be arranged in a rotatable or alternatively fixed manner on the telescopic rod 6.

Figure 3:
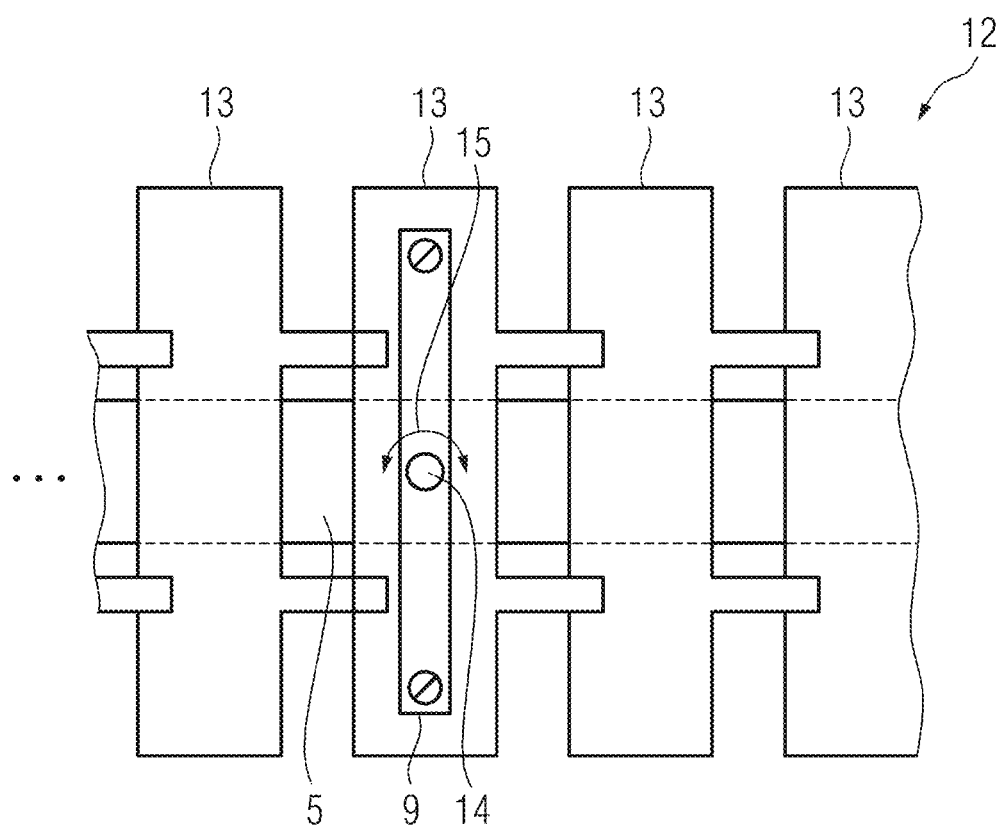
FIG. 3 shows a segment of an energy chain according to one or more example embodiments.

The lines 5 are preferably guided according to the representation in FIG. 3 in an energy chain 12, which has a multiplicity of chain links 13. The energy chain 12 encloses the lines 5 at least over 180°, preferably over at least 270°, and particularly preferably over their entire circumference. FIG. 3 shows only one line 5. A plurality of lines 5 can also be present however. It is also evident from FIG. 3 that the retaining elements 9 (this generally applies also to the further retaining elements 11) each retain at least one chain link 13 of the energy chain 12. These chain links 13 are immovably arranged in the respective retaining elements 9 and 11. FIG. 3 denotes by 14 an attachment point to which the particular retaining element 9 is connected to the telescopic rod 6. If the further retaining elements 11 are also rotatably arranged, this also applies to the further retaining elements 11. The rotatability is indicated by a double-ended arrow 15 in FIG. 3.

The travel of the CT installation 3 from the first installation limit position (shown in continuous lines in FIG. 1) into the second installation limit position (shown in dashed lines in FIG. 1) is explained below in connection with FIGS. 4 to 13.

Figure 4:
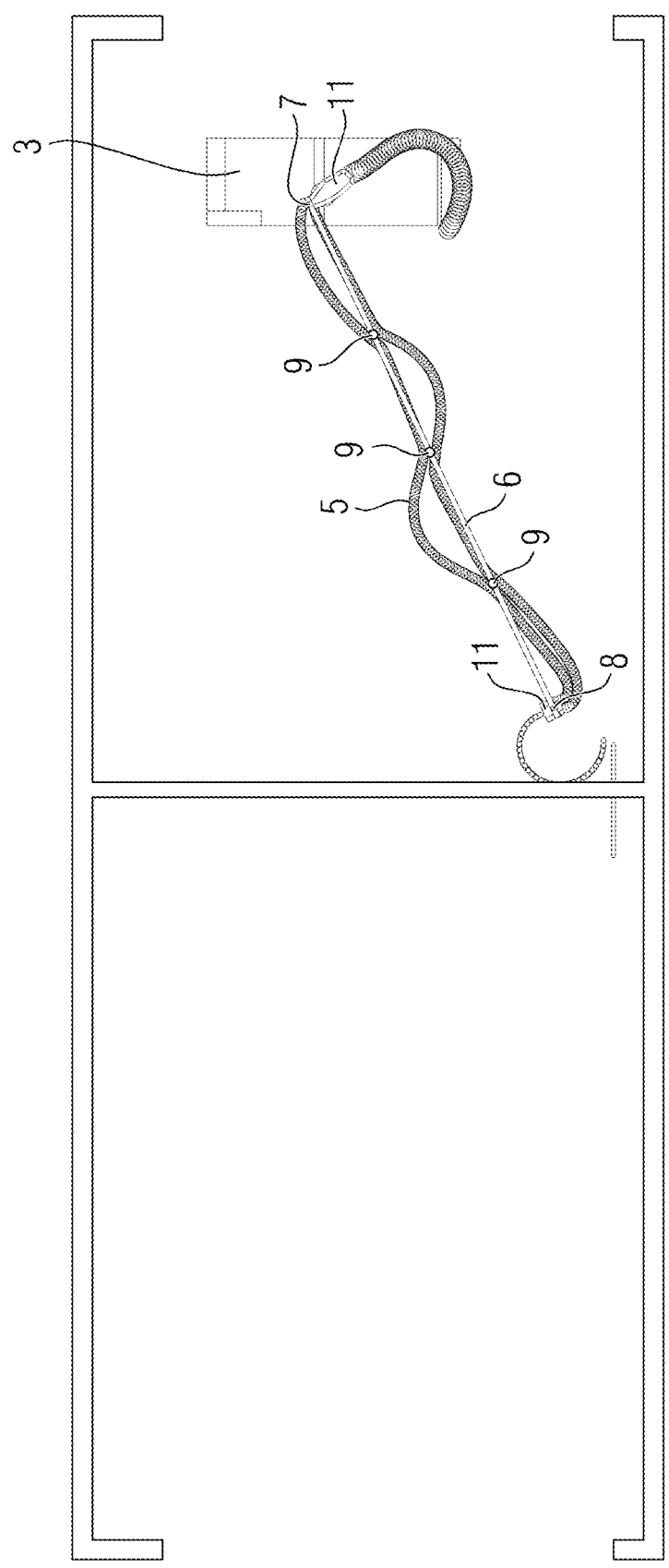

In the representation of FIG. 4, the CT installation 3 is in the first installation limit position. The telescopic rod 6 has its maximum length; the loops 10 of the lines 5 are relatively stretched out.

Figure 5:
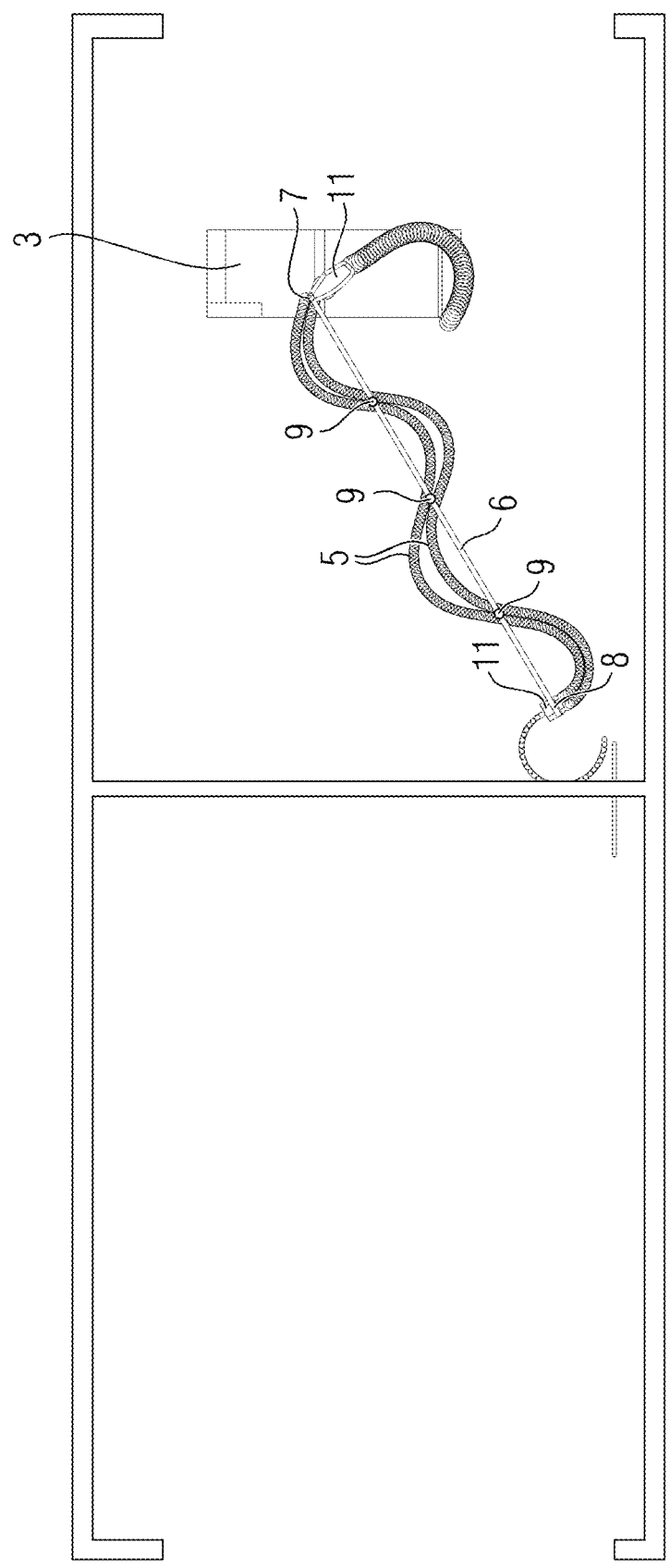

In the representation of FIG. 5, the CT installation 3 has been moved a little (still by a relatively small amount) from the first installation limit position towards the second installation limit position. The telescopic rod 6 is retracted a little (still by a relatively small amount); the loops 10 stretched out only slightly less.

Figure 6:
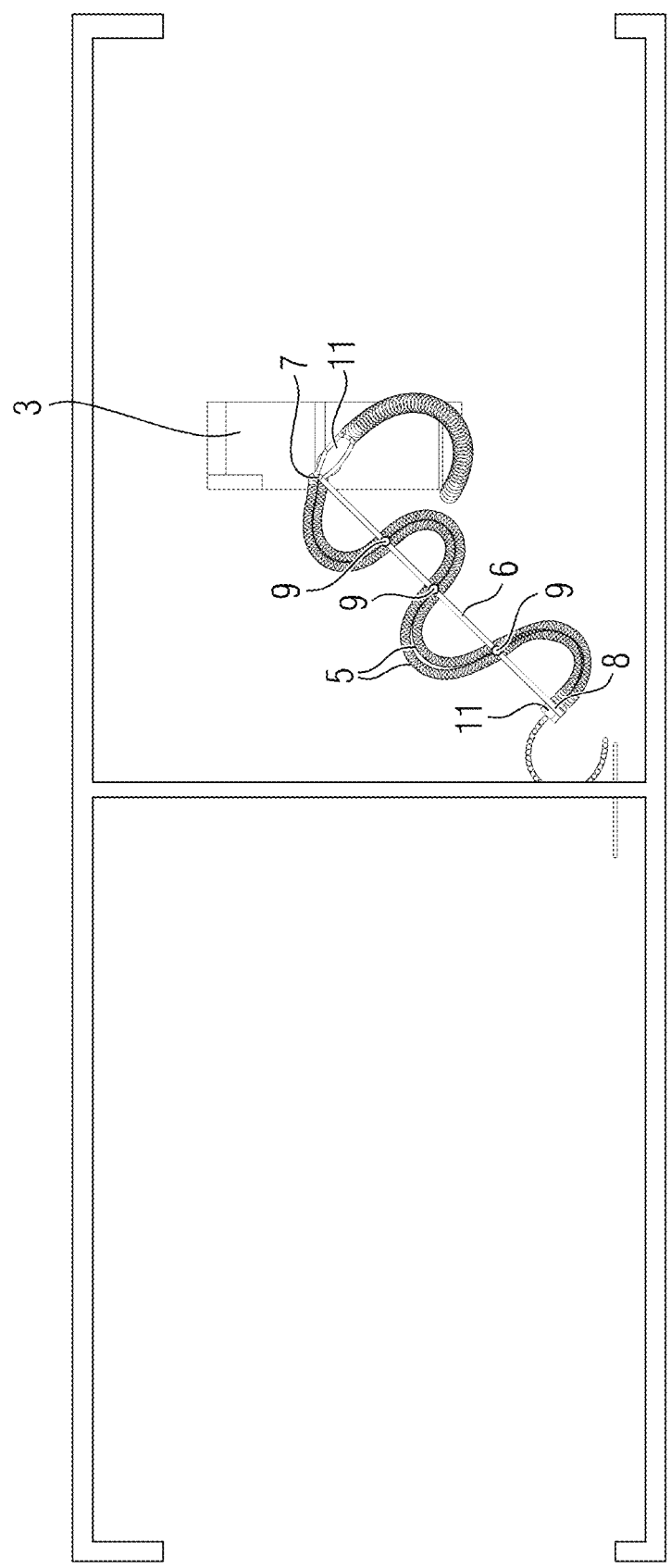

In the representation of FIG. 6, the CT installation 3 has been moved even further from the first installation limit position towards the second installation limit position. The telescopic rod 6 is retracted even further, the loops 10 stretched out even less.

In the representation of FIG. 7, the CT installation 3 has passed through about half the travel path from the first installation limit position to the second installation limit position. The telescopic rod 6 reached its minimum length shortly before. At this point in time it was oriented orthogonal to the direction of travel of the CT installation 3. The loops 10 have their minimum length (viewed in the direction of the axis of the telescopic rod 6), i.e. are only stretched out as little as possible.

In the representation of FIG. 8, the CT installation 3 has been moved even further from the first installation limit position towards the second installation limit position. The telescopic rod 6 is already extended again a little; the loops 10 are again slightly more stretched out than in the state in FIG. 7.

In the representation of FIG. 9, compared with the representation of FIG. 8, the CT installation 3 has been moved a little further still from the first installation limit position towards the second installation limit position. The telescopic rod 6 is extended yet a little more than in the representation of FIG. 8; the loops 10 are stretched out even slightly more than in the state in FIG. 8.

In the representation of FIG. 10, compared with the representation of FIG. 9, the CT installation 3 has not been moved further from the first installation limit position towards the second installation limit position. The CT installation 3 has been rotated, however, through approximately 90° about a vertical axis 16 (cf. FIG. 2). The vertical axis 16 usually runs exactly, or at least approximately, through the isocenter of the CT installation 3.

Also in the representation of FIG. 11, compared with the representation of FIG. 9, the CT installation 3 has not been moved further from the first installation limit position towards the second installation limit position. Compared with the representation in FIG. 10, however, the CT installation 3 has been rotated through approximately a further 90° about the vertical axis 16, i.e. through approximately 180° (preferably exactly through 180°) compared with the representation in FIG. 9.

In the representation of FIG. 12, compared with the representation in FIG. 11, the CT installation 3 has been moved further from the first installation limit position towards the second installation limit position. The telescopic rod 6 is extended slightly further; the loops 10 are stretched out even more than in the state in FIGS. 9 to 11.

In the representation of FIG. 13, the CT installation 3 has reached the second installation limit position. The telescopic rod 6 is again extended to a maximum extent; the loops 10 are stretched out to a maximum extent.

When the CT installation 3 travels from the second installation limit position into the first installation limit position, the inverse procedure is followed.

The procedure shown in FIGS. 4 to 13 is preferably followed when the CT installation 3 is meant to be operated in both installation limit positions. If the CT installation 3 is meant to be operated only in one of the two installation limit positions, the rotation of the CT installation 3 about the vertical axis 16 can be omitted. It can also be present in this case, however.

It is evident in FIG. 2 and FIGS. 4 to 13 that the lines 5 extend from the proximal hinge point 7 in a further loop 17 to an end point 18 that is fixed with respect to the CT installation 3. The further loop 17 is a direct continuation of the loop 10 adjacent to the proximal hinge point 7. Depending on the location of the CT installation 3 along the travel path from the first installation limit position to the second installation limit position, the further loop 17 may be curved in the same direction as, or in the other direction from, the loop 10 adjacent to the proximal hinge point 7. For example, a curvature in the same direction is the case in the state shown in FIG. 6. A curvature in the other direction is the case in the state in FIG. 12, for example. It is also evident in FIG. 2 and FIGS. 4 to 13 that the lines 5 extend also from the distal hinge point 8 in a further loop 19 to a further end point 20.

In the context of the procedure explained above in connection with FIGS. 4 to 13, the distal hinge point 8 can travel relative to the examination room 1 parallel to the travel path of the CT installation 3 between two hinge-point limit positions. A distance of travel between the two hinge-point limit positions, however, is clearly smaller than a distance of travel between the two installation limit positions. For example, the distance of travel of the CT installation 3 between the two installation limit positions can equal approximately 12 m to approximately 15 m, whereas the distance of travel of the distal hinge point 8 can lie in the range between 3 m and 6 m.

Furthermore, as an alternative to the distal hinge point 8 being able to travel by a relatively small amount, it is equally possible to arrange the distal hinge point 8 such that it is fixed relative to the examination room 1.

In summary, the present invention thus relates to the following substantive matter:

Arranged in an examination room 1 is a CT installation 3 which can travel along a predetermined travel path between two installation limit positions. Arranged on the CT installation 3 is a telescopic rod 6, which extends from a hinge point 7 that is proximal with respect to the CT installation 3 to a hinge point 8 that is distal with respect to the CT installation 3. The telescopic rod 6 is rotatably mounted in the two hinge points 8, 9 and can telescope between a minimum length and a maximum length. Arranged on the telescopic rod 6 are a number of retaining elements 9 that can travel along the telescopic rod 6. A number of lines 5 are guided via the retaining elements 9, so that when the telescopic rod 6 is of minimum length, the lines 5 are guided in serpentine loops 10.

The present invention has many advantages. For instance, in particular it can be implemented at low cost. In addition, the telescopic rod 6 is often universally usable. At any rate, just a few different telescopic rods 6 are required even for different embodiments having significantly different travel paths between the installation limit positions of the CT installation 3. There is no need to install a (large and heavy) ceiling box. In addition, a vertical pillar beside the gantry of the CT installation 3 is no longer needed. All parts are readily accessible and easy to clean. Inside the energy chain 12, interfaces, at which a leak, cable breaks, contact-making difficulties or other problems might occur, are no longer required for the lines 5. The lines 5 and also the energy chain 12 can be located in the installation limit positions always behind the CT installation 3, so that a disturbance in the laminar air flow in front of the CT installation 3 can be avoided.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device. The expression "a number of" has to be understood as "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the invention has been illustrated and described in detail using one or more example embodiments, the invention is not limited by the disclosed examples, and a person skilled in the art can derive other variants therefrom without departing from the scope of protection of the invention.

The invention claimed is:

1. An examination room, comprising:
    a computed tomography (CT) installation which can travel along a predetermined travel path between two installation limit positions;
    a telescopic rod on the CT installation, the telescopic rod extending from a hinge point that is proximal with respect to the CT installation to a hinge point that is distal with respect to the CT installation,
        wherein the telescopic rod is rotatably mounted in the two hinge points and can telescope between a minimum length and a maximum length;
    a number of retaining elements on the telescopic rod that can travel along the telescopic rod; and
    a number of lines are guided via the retaining elements such that when the telescopic rod is of the minimum length, the lines are guided in serpentine loops.

2. The examination room of claim 1, wherein the lines comprise at least one of
    supply lines for at least one of electrical energy, gas, liquid media, or
    at least one of electrical signal lines, optical signal lines or data lines.

3. The examination room of claim 1, wherein the lines are guided in an energy chain having a multiplicity of chain links.

4. The examination room of claim 3, wherein the retaining elements each retain at least one chain link of the energy chain, and the chain links are immovably arranged in the respective retaining elements.

5. The examination room of claim 1, wherein relative to the examination room, the distal hinge point is fixed or else can travel parallel to the travel path of the CT installation, a distance of travel between two hinge-point limit positions is smaller than a distance of travel between the two installation limit positions.

6. The examination room of claim 1, wherein the lines cross the telescopic rod in a region of the retaining elements, and the retaining elements are rotatably arranged on the telescopic rod.

7. The examination room of claim 6, wherein further retaining elements are arranged in the two hinge points, and the further retaining elements are arranged in a rotatable or fixed manner on the telescopic rod.

8. The examination room of claim 1, wherein between the two installation limit positions, the CT installation is rotatable about a vertical axis.

9. The examination room of claim 1, wherein the lines extend from the proximal hinge point in a further loop to an end point that is fixed with respect to the CT installation.

10. The examination room of claim 2, wherein the lines are guided in an energy chain having a multiplicity of chain links.

11. The examination room of claim 10, wherein the retaining elements each retain at least one chain link of the energy chain, and the chain links are immovably arranged in the respective retaining elements.

12. The examination room of claim 2, wherein relative to the examination room, the distal hinge point is fixed or else can travel parallel to the travel path of the CT installation, a distance of travel between two hinge-point limit positions is smaller than a distance of travel between the two installation limit positions.

13. The examination room of claim 2, wherein the lines cross the telescopic rod in a region of the retaining elements, and the retaining elements are rotatably arranged on the telescopic rod.

14. The examination room of claim 13, wherein further retaining elements are arranged in the two hinge points, and the further retaining elements are arranged in a rotatable or fixed manner on the telescopic rod.

15. The examination room of claim 2, wherein between the two installation limit positions, the CT installation is rotatable about a vertical axis.

16. The examination room of claim 2, wherein the lines extend from the proximal hinge point in a further loop to an end point that is fixed with respect to the CT installation.

17. The examination room of claim 3, wherein relative to the examination room, the distal hinge point is fixed or else can travel parallel to the travel path of the CT installation, a distance of travel between two hinge-point limit positions is smaller than a distance of travel between the two installation limit positions.

18. The examination room of claim 3, wherein the lines cross the telescopic rod in a region of the retaining elements, and the retaining elements are rotatably arranged on the telescopic rod.

19. The examination room of claim 18, wherein further retaining elements are arranged in the two hinge points, and the further retaining elements are arranged in a rotatable or fixed manner on the telescopic rod.

20. The examination room of claim 3, wherein between the two installation limit positions, the CT installation is rotatable about a vertical axis.

* * * * *

UNITED STATES PATENT AND TRADEMARK OFFICE
CERTIFICATE OF CORRECTION

PATENT NO.         : 11,959,570 B1
APPLICATION NO.    : 18/476639
DATED              : April 16, 2024
INVENTOR(S)        : Moritz Weber et al.

It is certified that error appears in the above-identified patent and that said Letters Patent is hereby corrected as shown below:

On the Title Page

Item (73), should read as follows:
(73) Assignee: SIEMENS HEALTHINEERS AG, Forchhein (DE)

Insert:
--(65) Prior Publication Data
US 2024/0110639-A1 April 4, 2024--

Signed and Sealed this
Fifteenth Day of July, 2025

Coke Morgan Stewart
*Acting Director of the United States Patent and Trademark Office*